United States Patent [19]
Moore et al.

[11] Patent Number: 5,337,758
[45] Date of Patent: Aug. 16, 1994

[54] SPINE MOTION ANALYZER AND METHOD

[75] Inventors: Robert R. Moore, Hayward; Steve R. Lamb, Pleasanton; Larry W. Lamoreux, Lafayette; Michael H. McTeigue, Mountain View, all of Calif.

[73] Assignee: Orthopedic Systems, Inc., Hayward, Calif.

[21] Appl. No.: 640,490

[22] Filed: Jan. 11, 1991

[51] Int. Cl.⁵ .............................................. A61B 5/11
[52] U.S. Cl. .................................. 128/781; 128/782; 273/190 R
[58] Field of Search ................. 128/774–782; 273/188 R, 190 R, 190 C, 183 R, 183 B, DIG. 17, DIG. 19, 187.2; 434/258

[56] References Cited

U.S. PATENT DOCUMENTS

| | | | |
|---|---|---|---|
| 4,306,571 | 12/1981 | McLeod, Jr. | 128/782 |
| 4,493,328 | 1/1985 | Saito | 128/782 |
| 4,571,834 | 2/1986 | Fraser et al. | 33/1 PT |
| 4,646,754 | 3/1987 | Seale | 128/774 |
| 4,660,829 | 4/1987 | Whiteneir | 273/29 A |
| 4,800,897 | 1/1989 | Nilsson | 128/782 |
| 4,912,638 | 3/1990 | Pratt, Jr. | 364/413.02 |
| 5,012,819 | 5/1991 | Marras et al. | 128/781 |
| 5,067,717 | 11/1991 | Harlan et al. | 273/183 B |
| 5,094,249 | 3/1992 | Marras et al. | 128/781 |

*Primary Examiner*—Angela D. Sykes
*Attorney, Agent, or Firm*—Flehr, Hohbach, Test, Albritton & Herbert

[57] ABSTRACT

Spine motion analyzer and method in which a self-aligning measurement linkage is attached to the subject above and below the portion of the spine in which motion is to be monitored. Mounts are provided for attaching the ends of the linkage in fixed positions near the sacrum, beneath the scapulae, and on the head for monitoring either lumbar motion or cervical motion. The linkage has a plurality of arms which move relative to each other in accordance with movement of the spine between the points to which the linkage is attached, and transducers connected to the linkage arms provide electrical signals which can be processed to provide video, printed and/or auditory indications of the spinal movements. One embodiment, which is particularly adapted for sports testing such as golf swing analysis includes a transducer such as a gyroscope which permits measurements to be taken with respect to an absolute or fixed reference such as the ground.

10 Claims, 13 Drawing Sheets

SPINE MOTION ANALYZER AND METHOD

BACKGROUND OF THE INVENTION

This invention pertains generally to the analysis of spinal movement and, more particularly, to a spine motion analyzer and method which can simultaneously monitor all rotations of the cervical spine and/or the lumbar spine and provide a relatively complete biomechanical assessment of spinal motion.

The analysis of spinal motion can provide valuable information in the diagnosis and treatment of both complex and simple spinal problems. It is also useful in other clinical applications such as determining how a patient is progressing in the recovery from an injury or how he is progressing in a physical therapy program. Being something which is difficult to manipulate, spinal motion can provide a very revealing indication of the true condition of accident victims or other people who have suffered, or claim to have suffered, spinal injury.

The analysis of spinal motion can also be helpful in developing sports techniques such as the swinging of a golf club, a tennis racket or a baseball bat, or the throwing of a ball.

One technique heretofore employed in the analysis of spinal motion is visual observation. This technique is of relatively limited value, however, due to the limitations of the human eye and other visual techniques and the inability to detect certain movements or to accurately measure the speed, smoothness and symmetry of movements, which can be more significant than static measurements in evaluating the biomechanical action of the spine.

Another technique heretofore employed utilizes photodetectors to monitor light reflected from targets attached to the patient along the spine and to provide electrical signals which are processed to provide graphical analyses of spinal movement.

It is in general an object of the invention to provide a new and improved apparatus and method for analyzing spinal movement.

Another object of the invention is to provide a spine motion analyzer and method of the above character which overcome the limitations and disadvantages of techniques heretofore employed in analyzing spinal motion.

Another object of the invention is to provide a spine motion analyzer and method of the above character which can simultaneously monitor all rotations of the cervical spine and/or the lumbar spine and provide a relatively complete biomechanical assessment of spinal motion.

Another object of the invention is to provide a spine motion analyzer and method of the above character which are useful in developing sports techniques such as the swinging of a golf club, a tennis racket or a baseball bat, or the throwing of a ball.

These and other objects are achieved in accordance with the invention by the use of a self-aligning measurement linkage which is attached to the subject above and below the portion of the spine in which motion is to be monitored. Mounts are provided for attaching the ends of the linkage in fixed positions near the sacrum, beneath the scapulae, and on the head for monitoring either lumbar motion or cervical motion. The linkage has a plurality of arms which move relative to each other in accordance with movement of the spine between the points to which the linkage is attached, and transducers connected to the linkage arms provide electrical signals which can be processed to provide video, printed and/or auditory indications of the spinal movements. One embodiment, which is particularly adapted for sports testing such as golf swing analysis includes a transducer such as a gyroscope which permits measurements to be taken with respect to an absolute or fixed reference such as the ground.

DETAILED DESCRIPTION OF THE PREFERRED EMBODIMENTS

Figure 1:
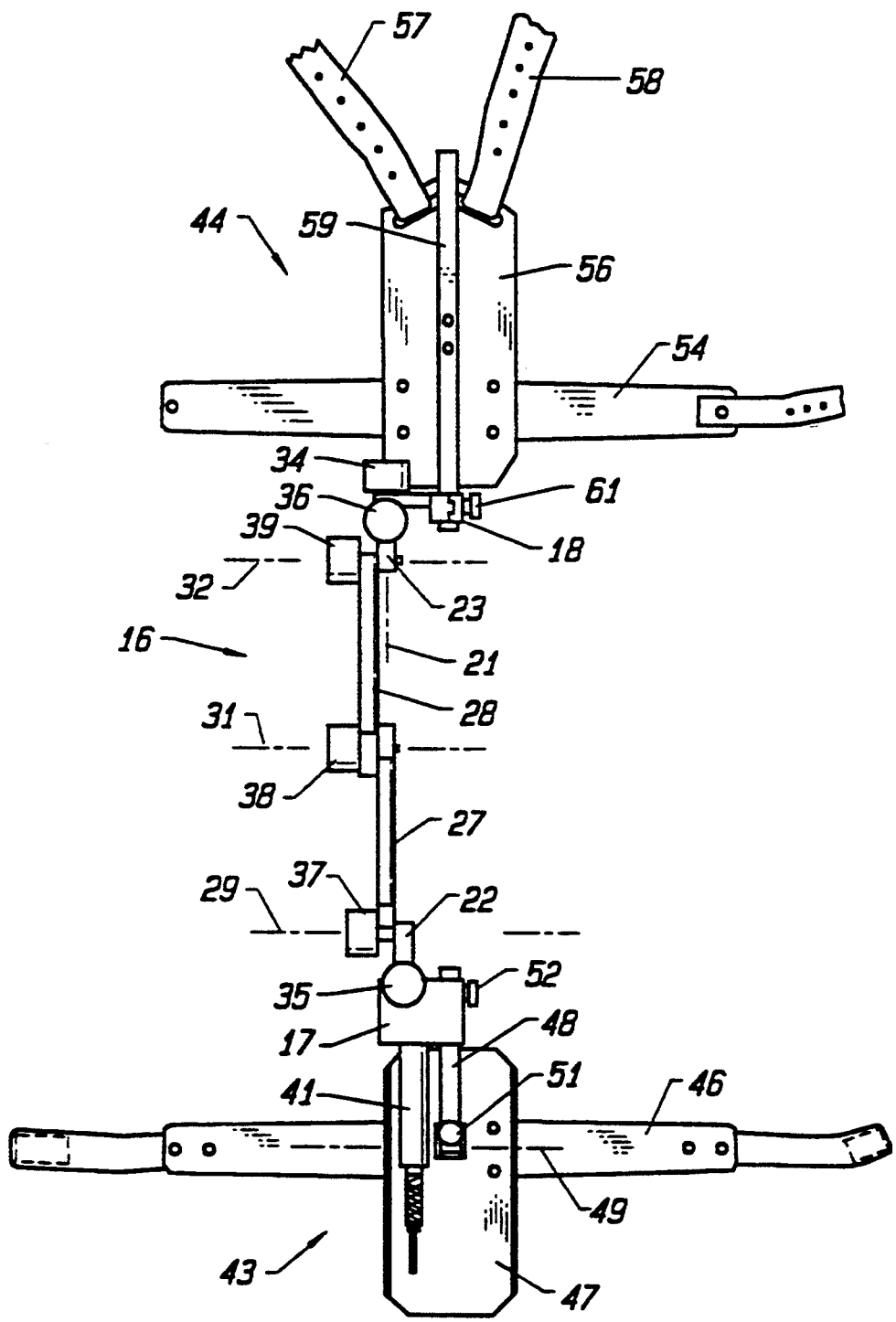
FIG. 1 is a plan view of one embodiment of a measurement linkage with mounts for monitoring lumbar spinal motion in accordance with the invention.

The spine motion analyzer includes a measurement linkage 16 which is attached to the body of the subject above and below the portions of the spine in which motion is to be monitored. As illustrated in the drawings, the linkage includes a base link or lower mounting block 17 and an upper link or mounting block 18 which, as discussed more fully hereinafter, are fixedly attached to mounts by which the linkage is attached to the subject for lumbar and cervical measurements. A short arm 19 is pivotally connected to the upper mounting block for rotation about a vertically extending axis 21, and a first pair of arms 22, 23 are pivotally connected to the lower mounting block and to arm 19 for rotation about horizontally extending axes 24, 26 which are parallel to the sagittal plane of the subject. A second pair of arms 27, 28 are pivotally connected to the first pair of arms and to each other for rotation about horizontally extending axes 29, 31, 32 which are perpendicular to the sagittal plane.

Transducers are provided at the connections between the arms of the linkage for providing electrical signals corresponding to the positions of the arms and the portion of the spine to which the linkage is attached. A transducer 34 at the junction of upper mounting block 18 and arm 19 monitors rotation about vertically extending axis 21 and provides a signal corresponding to axial rotation of the spine. Transducers 35, 36 at the junction of lower mounting block 18 and arm 22 and the junction of arms 19 and 23 monitor rotation about horizontally extending axes 24, 26, respectively, and provide signals corresponding to lateral bending of the spine. Transducers 37, 38 and 39 at the junctions of arms 22 and 27, arms 27 and 28, and arms 28 and 23 monitor rotation about horizontally extending axes 29, 31 and 32, respectively, and provide signals corresponding to extension and flexion of the spine.

In the embodiment illustrated, transducers 34-39 are rotary potentiometers which provide electrical resistances corresponding to the relative positions of the arms connected thereto. In this embodiment, the mechanical connections between the arms are made through the potentiometers, with the body of each potentiometer being affixed to one arm and the shaft being affixed to another. However, it will be understood that any other suitable types of transducers and connections between the arms can be employed, if desired.

When reference voltages are applied to the potentiometers, the potentiometers provide electrical signals in the form of output voltages corresponding to the relative positions of the linkage arms to which the potentiometers are connected. These voltages are monitored to determine the position and movement of the spine, and changes in the voltages are monitored to determine the velocity of spinal movement. Electrical connections to the potentiometers are made by means of electrical leads (not shown) which pass through the arms of the linkage, with a connecting cable 41 extending between lower mounting block 17 and the signal processing equipment (not shown).

Linkage 16 is one form of a linkage sometimes called a six bar linkage for monitoring six degrees of freedom of motion in three dimensional space. This particular linkage has arms of fixed length with six pivotal joints with rotational transducers for monitoring three rotational motions and three translational motions. If desired, other types of measurement linkages can be utilized, e.g., a six bar linkage having one or more translational connections between its arms and a correspondingly lesser number of rotational connections.

Figure 2:
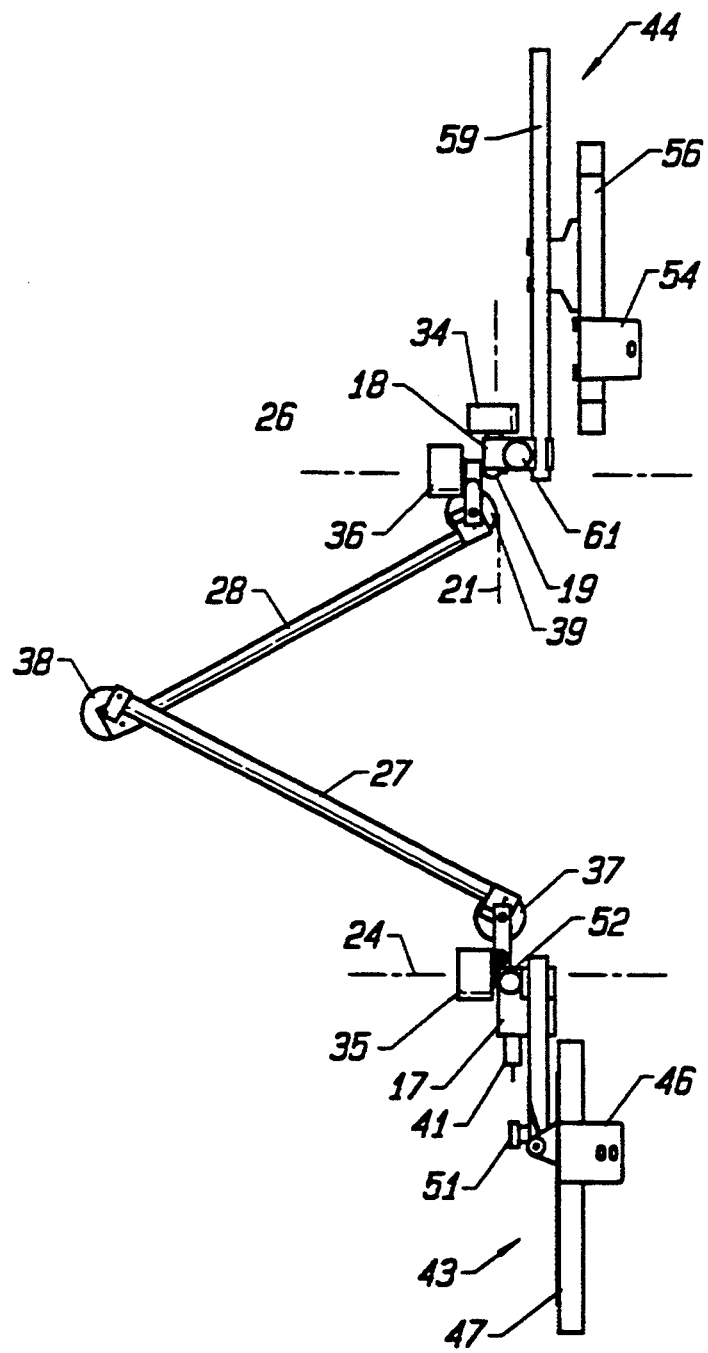
FIG. 2 is a side elevational view of the embodiment of FIG. 1.

In the embodiment of FIGS. 1 and 2, the linkage is shown in connection with a pelvic mount 43 and a thoracic mount 44 for attachment to the subject to measure movement of the lumbar spine. Mount 43 comprises a strap or belt 46 having a padded mounting plate 47 affixed thereto. A mounting post 48 is pivotally mounted on the plate for adjustment about a horizontally extending axis 49 to a vertical position, with a clamp 51 for holding the post in that position. The belt encircles the hips of the subject, with the mounting post centered over the sacrum. The mounting post fits into a bore in the lower mounting block 17, and the block is secured in a fixed position on the post by a set screw 52.

Mount 44 comprises a chest strap or belt 54 which has a padded mounting plate 56 affixed thereto. A pair of shoulder straps 57, 58 are connected to the mounting plate and are adapted to extend over the shoulders of the subject and connect to the chest strap on the front side of the subject. A vertically extending mounting post 59 is affixed to plate 56. The chest strap encircles the torso of the subject just below the scapulae, with mounting post 59 centered over the spine. The lower end portion of this post fits into a bore in upper mounting block 18, with a set screw 61 securing the block in a fixed position on the post.

Figure 3:
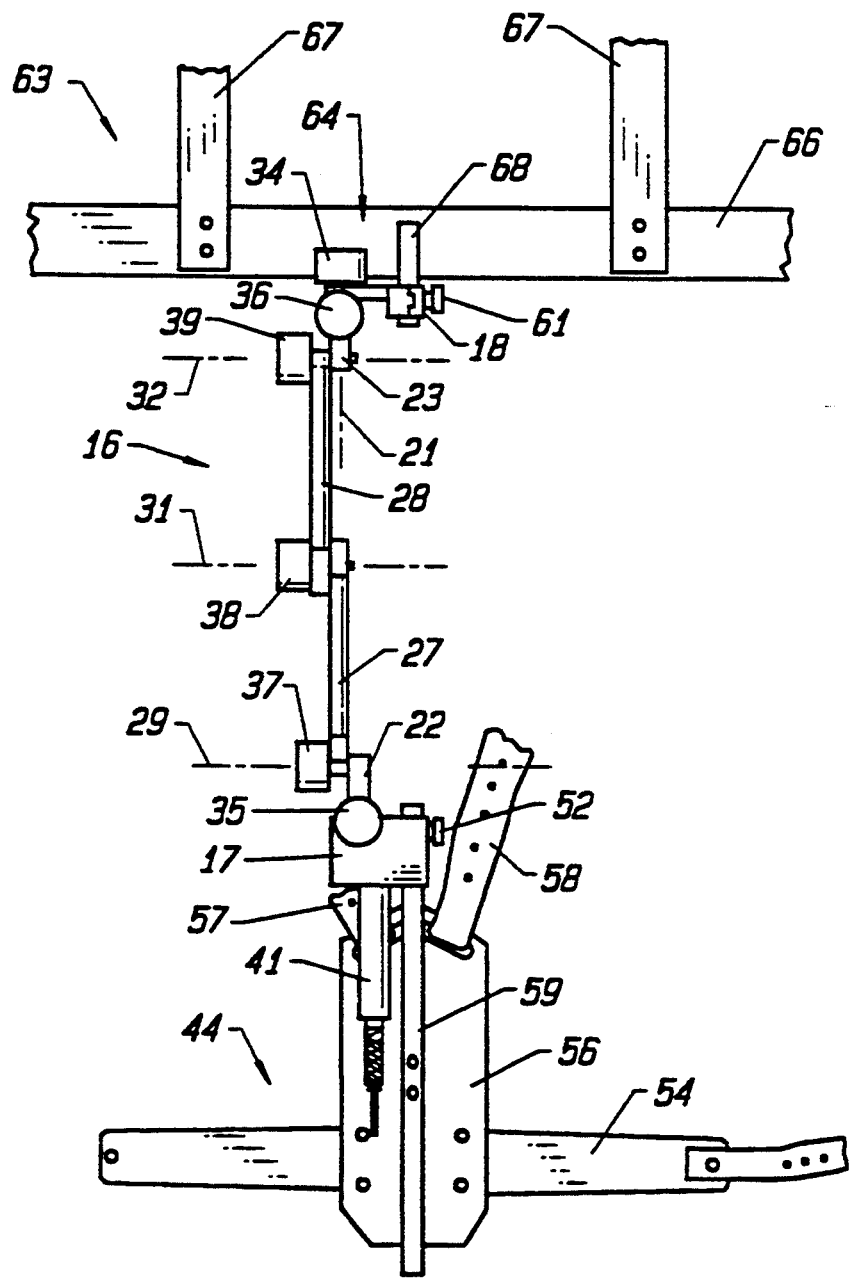
FIG. 3 is a plan view of the linkage of FIG. 1 with mounts for monitoring cervical spinal motion.
Figure 4:
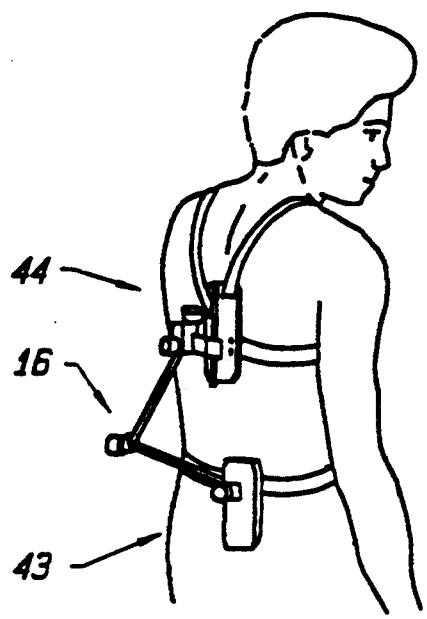
FIGS. 4–7 are operational views showing the use of the invention for monitoring different movements of the lumbar spine.
Figure 5:
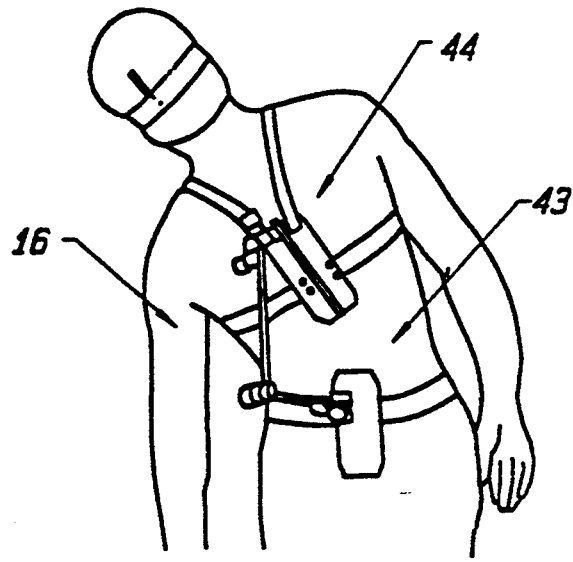
Figure 6:
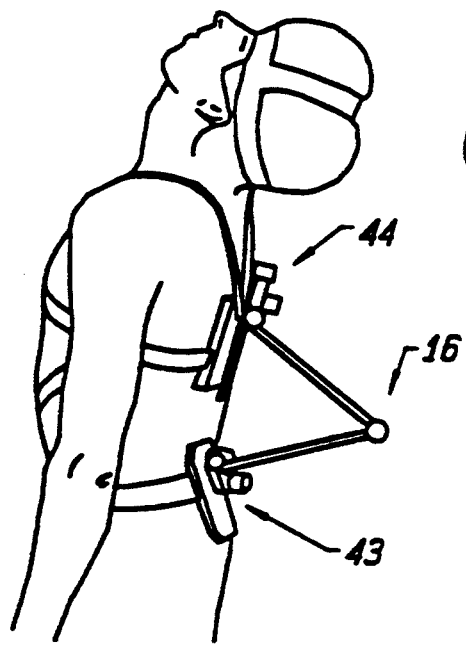
Figure 7:
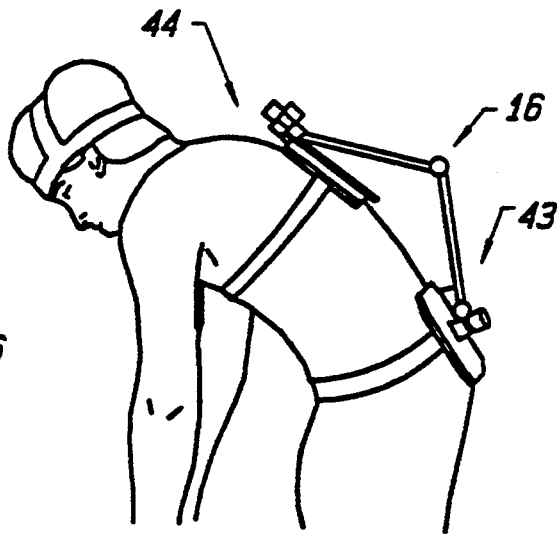
Figure 8:
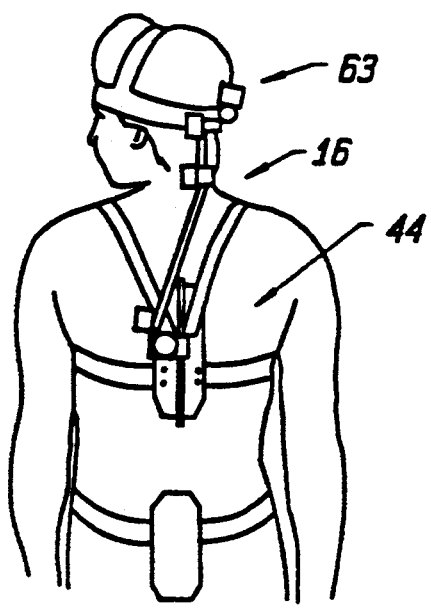
FIGS. 8–11 are operational views showing the use of the invention for monitoring different movements of the cervical spine.
Figure 9:
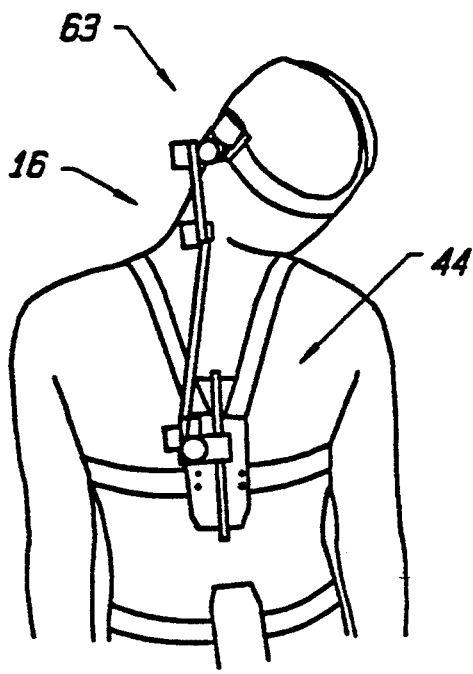
Figure 10:
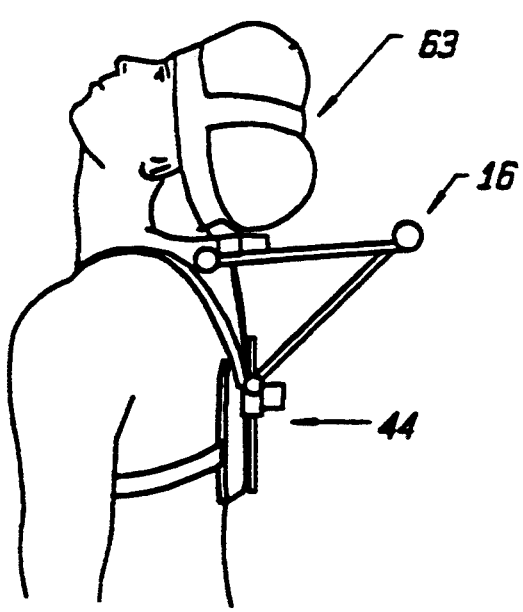
Figure 11:
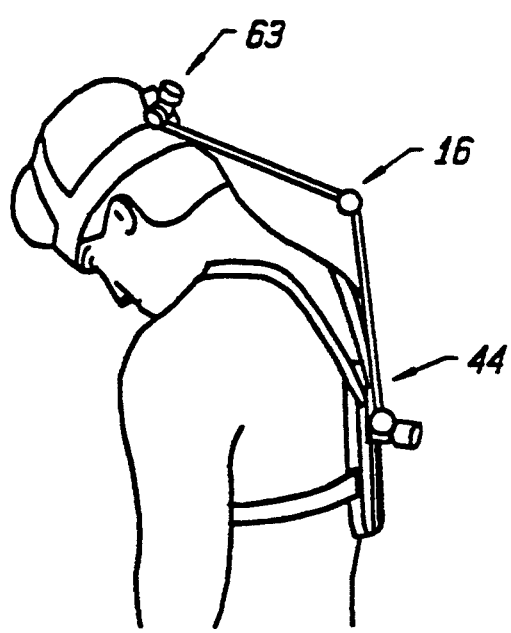

In FIG. 3, the linkage is illustrated in connection with thoracic mount 44 and a head mount 63 for monitoring cervical movement of the spine. In this embodiment, the thoracic mount is the same mount that holds the upper end of the linkage for lumbar measurements, except the lower end of the linkage is now attached to this mount, with lower mounting block 17 being mounted on the upper end portion of post 59 and set screw 52 securing the block in a fixed position on the post.

Mount 63 comprises a headgear 64 having a band 66 which encircles the head above the ears and a strap 67 which extends over the top of the head between opposite sides of the band. A downwardly extending mounting post 68 is affixed to the rear portion of the head band and is positioned in vertical alignment with the upper portion of the spine. This post fits into the bore in upper mounting block 18, with set screw 61 securing the block in a fixed position on the post.

Operation and use of the analyzer, and therein the method of the invention, can be described with reference to the operational views of FIGS. 4-11. For lumbar spinal measurements, the pelvic mount 43 is attached to the subject, with belt 46 encircling the hips and mounting post 48 centered over the sacrum. The post is adjusted to a vertical position, and clamp 51 is tightened. Thoracic mount 44 is attached to the subject, with chest strap encircling the subject's torso just below the scapulae. Shoulder straps 57, 58 are placed over the shoulders and attached to the chest strap in front side of the chest, with mounting post 59 centered over the spine. Mounting blocks 17, 18 are then placed on posts 48, 59, and set screws 52, 61 are tightened to secure the ends of the linkage in position.

With the linkage thus mounted on the lower portion of the subject's back and connected to the signal processing equipment, transducer 34 provides a signal corresponding to axial rotation of the lumbar spine, transducers 35, 36 provide signals corresponding to lateral bending of the lumbar spine, and transducers 37-39 provide signals corresponding to extension and flexion of the lumbar spine. Examples of such movements are illustrated in FIGS. 4-7, with right axial rotation in FIG. 4, left lateral bending in FIG. 5, extension FIG. 6 and flexion in FIG. 7. The signals produced by the transducers are processed to provide information about the range and rate of lumbar movement.

For cervical spinal measurements, thoracic mount 44 is attached to the subject, just as it is for lumbar measurements, and headgear 64 is attached to the head, with band 66 encircling the head above the ears, strap 67 extending over the top of the head, and mounting post 68 aligned with the upper portion of the spine. Mounting blocks 17, 18 are then placed on posts 59, 68, and set screws 52, 61 are tightened to secure the ends of the linkage in position. As noted above, lower mounting block 17 is mounted on the upper portion of thoracic mounting post 59 for cervical measurements, whereas upper mounting block 18 is mounted on the lower portion of this post for lumbar measurements.

With the linkage mounted on the upper portion of the subject's back and connected to the signal processing equipment, transducer 34 provides a signal corresponding to axial rotation of the cervical spine, transducers 35, 36 provide signals corresponding to lateral bending of the cervical spine, and transducers 37–39 provide signals corresponding to extension and flexion of the cervical spine. Examples of such movements are illustrated in FIGS. 8–11, with right axial rotation in FIG. 8, left lateral bending in FIG. 9, extension in FIG. 10, and flexion in FIG. 11. As in the case of lumbar measurements, the signals produced by the transducers are processed to provide information about the range and rate of cervical movement.

If simultaneous measurements of lumbar and cervical movement are desired, a pair of similar linkages can be employed, with one of the linkages being mounted between the pelvic mount and the thoracic mount and the other linkage being mounted between the thoracic mount and the headgear.

Figure 12:
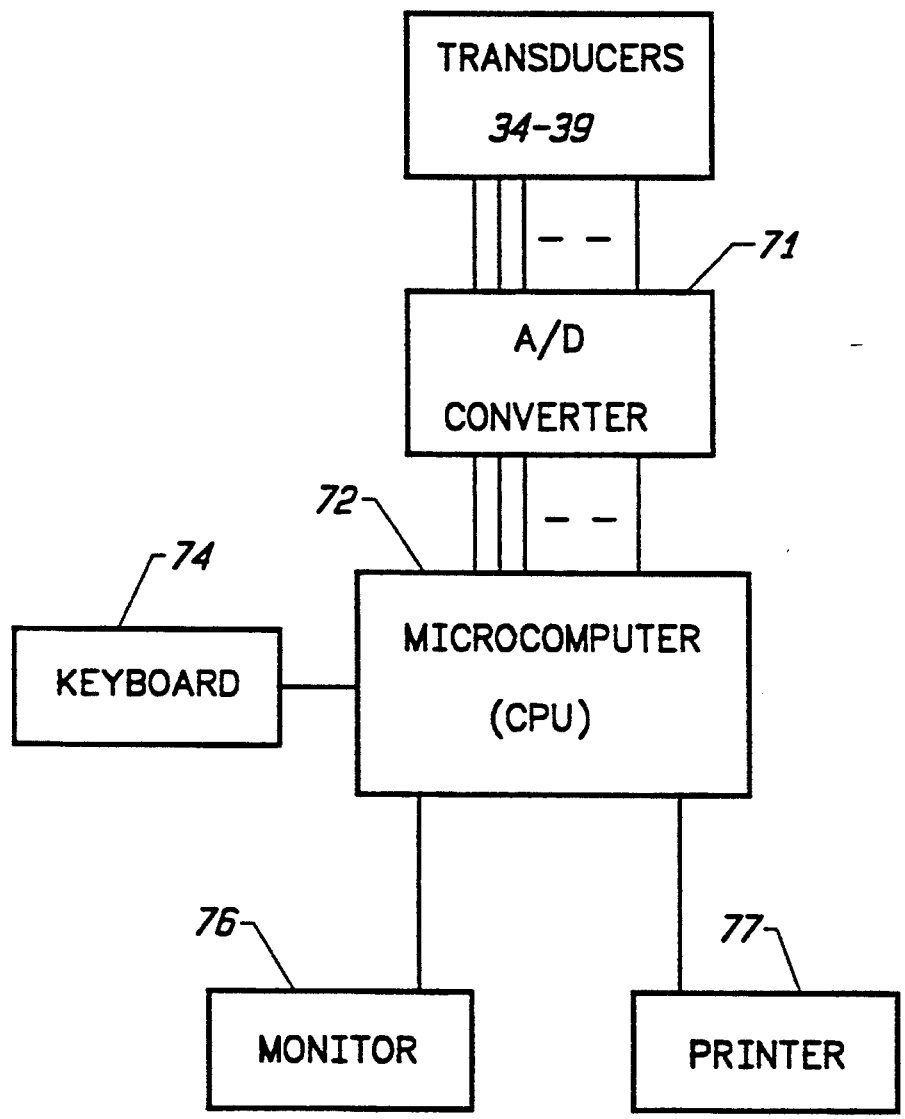
FIG. 12 is a block diagram of one embodiment of a system employing the linkage of FIG. 1 for analyzing spinal motion in accordance with the invention.

As illustrated in FIG. 12, the signals from the transducers are applied to an analog-to-digital (A/D) converter 71 connected to a computer 72. The computer can be of any suitable type, and in one presently preferred embodiment, a microcomputer of the type commonly known as an IBM compatible is employed. In this embodiment, the A/D converter is constructed on a board or card which is installed in one of the expansion slots of the computer. A keyboard 74, a video monitor 76 and a printer 77 are connected to the computer in the conventional manner.

A reference voltage is applied to each of the potentiometers which make up the transducers in the linkage, and each of the potentiometers produces an analog voltage corresponding to the relative angular positions of the two arms of the linkage to which it is connected. These voltages are converted to digital signals by the A/D converter.

When the linkage is manufactured, the potentiometers are calibrated by applying a reference voltage to the them and recording the relationship between the angular positions of the potentiometers and the digital signals corresponding thereto. In one presently preferred embodiment, the A/D converter has a range of 4096 increments for 360 degrees of potentiometer movement, which provides approximately 12 A/D increments per degree of rotation.

The data is normalized to eliminate any errors due to differences in the reference voltage by which the potentiometers are calibrated and the reference voltages in the systems in which the linkage is used. Thus, in one presently preferred embodiment, a calibration factor is obtained by multiplying the ratio of the potentiometer position to the A/D reading by the reference voltage of the calibrating system, i.e.

$$CF = \frac{POT}{ADI} \times V_{REF}$$

where CF is the calibration factor, POT is the position of the potentiometer in degrees, ADI is the reading of the A/D converter in increments, and $V_{REF}$ is the reference voltage of the calibration system. The calibration factors or multipliers also contain sign information corresponding to the relative directions in which the different potentiometers rotate during movement of the linkage, and this permits the angles measured by the different potentiometers to be combined by simple addition to determine the movement of the subject. The multiplier for potentiometer 34 which monitors axial rotation is assigned a negative sign. For the two potentiometers which monitor lateral bending, the multiplier for potentiometer 35 has a negative sign and the multiplier for potentiometer 36 has a positive sign. For the three potentiometers which monitor anterior-posterior bending, the multiplier for potentiometer 37 has a negative sign, and the multipliers for potentiometers 38, 39 have positive signs. The calibration factors or multipliers are stored in a data file which can be read into the computer with which measurements are made.

When making a measurement, the readings of the A/D converter for each potentiometer are multiplied by the calibration factor for the potentiometer and divided by the reference voltage of the computer with which the linkage is used to provide normalized data corresponding to the position of the potentiometer. Thus, $$ANGLE = \frac{CF}{V_{REF}} \times DATA$$

where ANGLE is the position of the potentiometer in degrees, CF is the calibration factor or multiplier, DATA is the reading of the A/D converter when a measurement is made, and $V_{REF}$ is the reference voltage of the computer with which the measurement is made.

The normalized data is processed to provide graphical and/or numerical representations of the movement of the subject, and examples of the graphical representations are shown in FIGS. 13–16. These particular examples show actual data for cervical movement of a subject having the linkage mounted on the upper portion of his back as illustrated in FIGS. 8–11.

Figure 13:
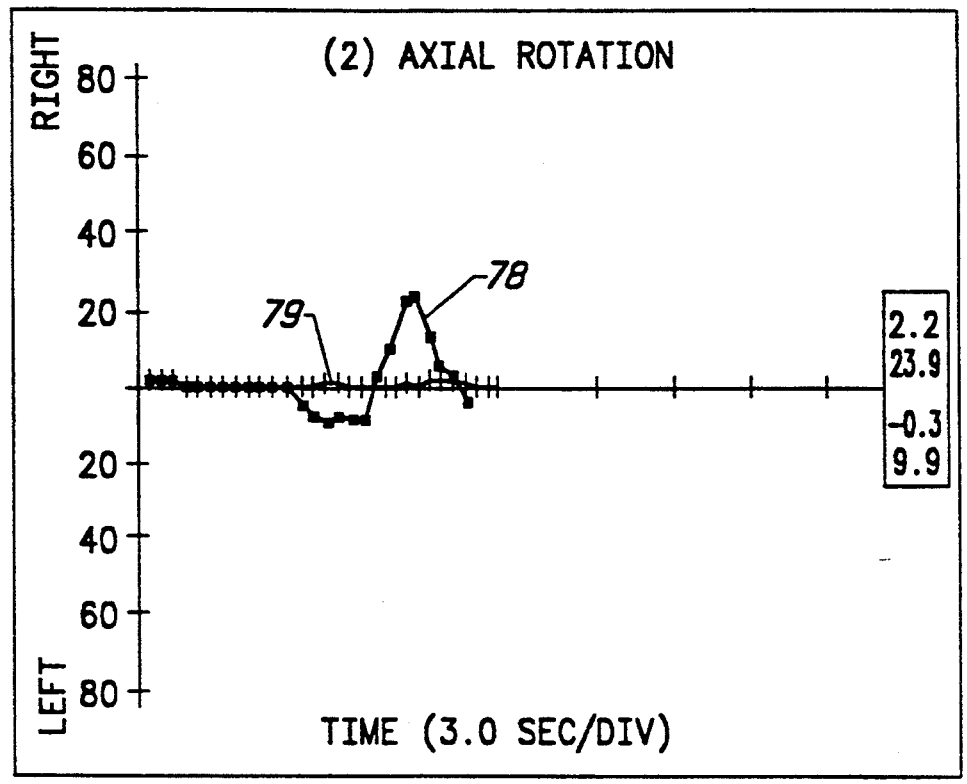
FIGS. 13–16 are examples of graphical representations in which spinal motion is displayed in the system of FIG. 12.

In the graph of FIG. 13, axial rotation is shown as a function of time. This graph actually includes two curves, one of which (curve 78) shows axial rotation associated with anterior-posterior cervical bending (flexion), the other of which (curve 79) shows axial rotation associated with cervical lateral bending. Axial rotation is plotted in 10-degree increments along the vertical axis, with right rotation being shown in the positive direction and left rotation being shown in the negative direction. Time is plotted in 3-second increments along the horizontal axis. The data points for curve 78 are indicated by squares, and the data points for curve 79 are indicated by crosses. As curve 78 shows, the subject exhibited significant right and left axial rotation when bending laterally, but almost no axial rotation when bending forward and back.

Figure 14:
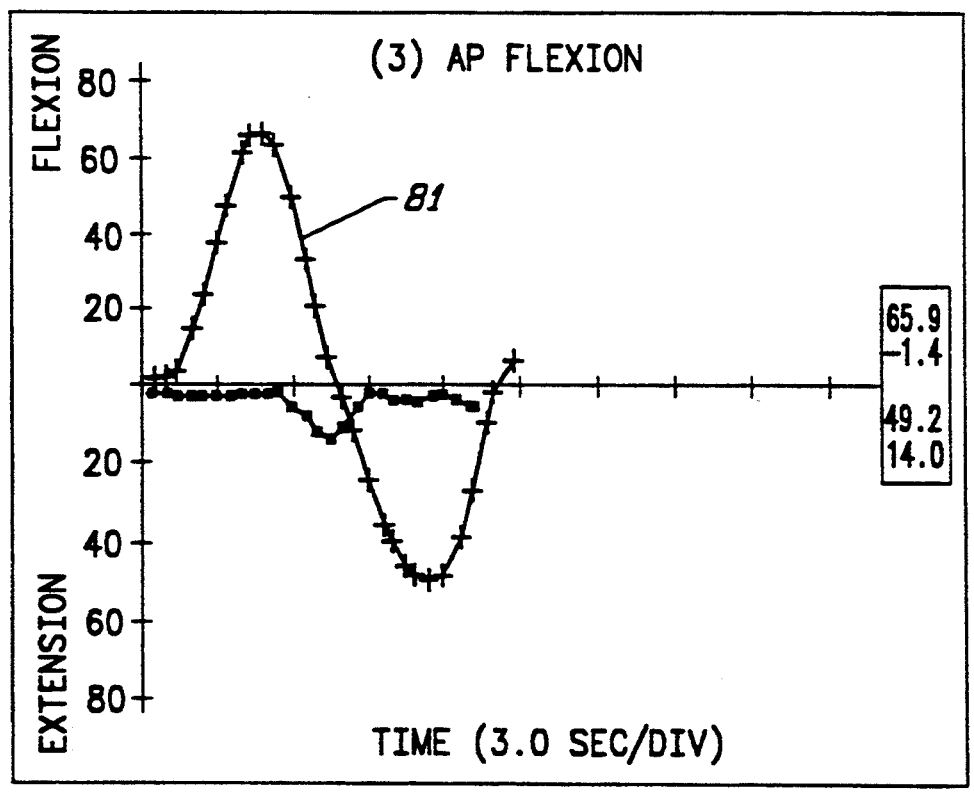

In the graph of FIG. 14, curve 81 shows anterior-posterior bending (flexion) as a function of time, and curve 82 shows lateral bending associated with the anterior-posterior bending. Flexion and lateral bending are plotted in 20-degree increments along the vertical axis, with forward bending (flexion) and right lateral bending being shown in the positive direction and backward bending (extension) and left lateral bending being shown in the negative direction. Time is plotted in 3-second increments along the horizontal axis. The negative peak in curve 82 shows that in this particular example, as the subject returned toward an upright position from anterior bending (flexion), there was also some lateral bending toward the left. During extension, however, there was no significant lateral bending.

Figure 15:
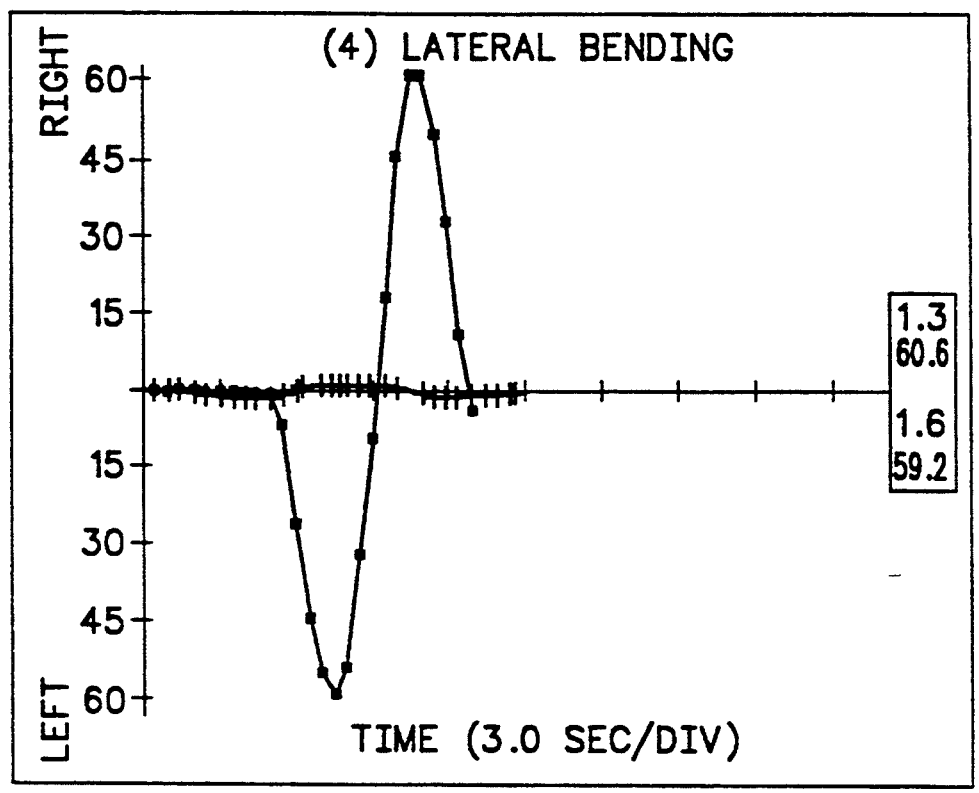

In FIG. 15, curve 83 shows lateral bending as a function of time, and curve 84 shows anterior-posterior bending associated with the lateral bending. Lateral bending and flexion are plotted in 15-degree increments along the vertical axis, with right lateral bending and anterior flexion being shown in the positive direction and left lateral bending and posterior flexion (extension) being shown in the negative direction. Time is plotted in 3-second increments along the horizontal axis. In this example, the curves show that there was very little forward and backward bending as the subject bent to the sides.

Figure 16:
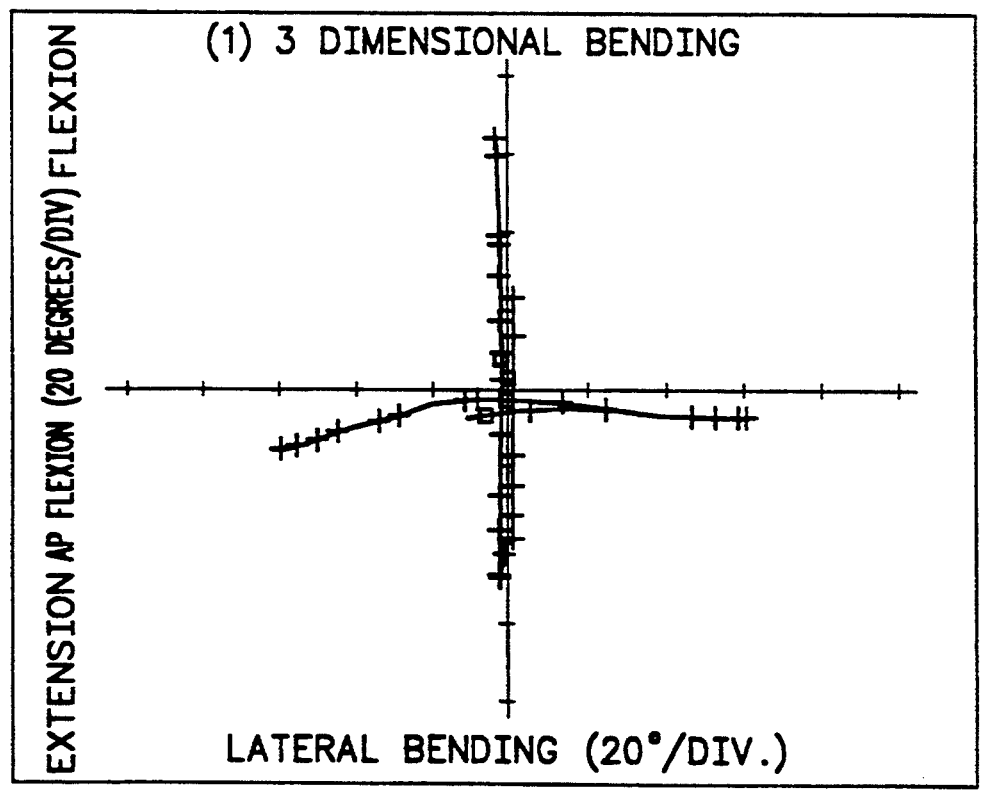

The graph in FIG. 16 shows a combination of anterior-posterior bending, lateral bending, and axial rotation, with anterior-posterior bending being plotted along the vertical axis, lateral bending being plotted along the horizontal axis, and axial rotation being indicated by the rotational position of the crosses representing the data points in the plots of anterior-posterior bending and lateral bending. In this particular example, the subject bent forward and backward and from side to side. There was relatively little lateral bending or axial rotation during flexion and extension, but there was some axial rotation and extension associated with the lateral bending, particularly near the left extreme of the lateral bending.

Graphical representations of the type shown in FIGS. 13-16 can be displayed on the monitor 76 and printed by the printer 77. In one presently preferred embodiment, all four of the graphs can be displayed simultaneously in separate windows on the monitor screen, or they can be displayed individually on a larger scale in a single window.

Figure 17:
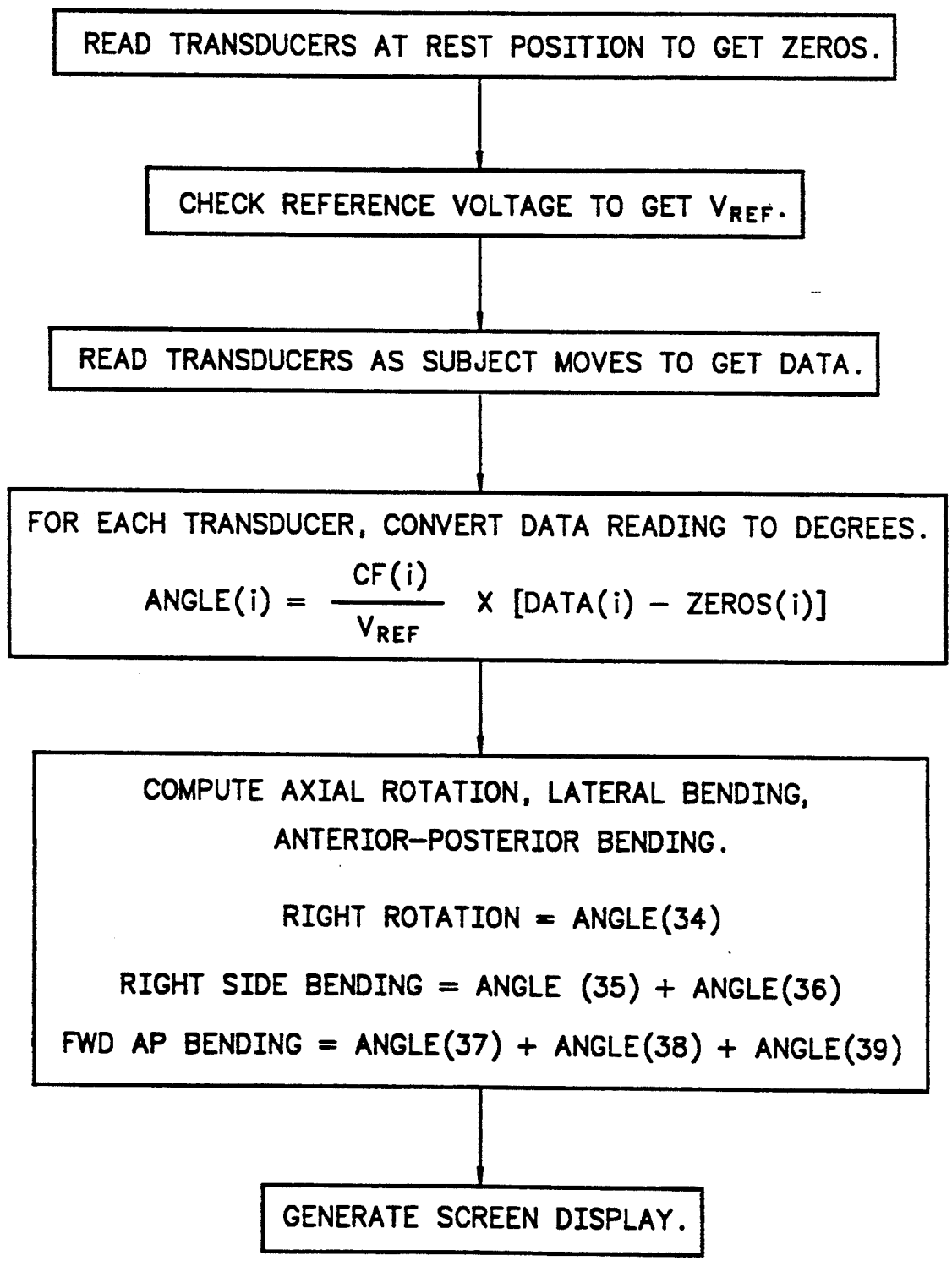
FIG. 17 is a flow chart illustrating one embodiment of a process for processing data to determine spinal motion in accordance with the invention.

The manner in which the data from the transducers is processed to produce the graphical representations is illustrated in the flow chart of FIG. 17. With the linkage mounted on the subject and the subject at rest in an upright or erect position, the potentiometers are scanned by reading the data from the A/D converter for successive ones of the potentiometers to provide a zero reference value ZEROS(i) for each of them. These values are stored in the memory of the computer. The reference voltage $V_{REF}$ for the system is checked by subtracting the computer's ground voltage from its high voltage, and this value is also stored.

As the subject moves, the output of the A/D converter is scanned repeatedly to read the potentiometers and thereby collect the data for the measurement. The data DATA(i) for each potentiometer is adjusted in accordance with the zero reference value and converted from A/D increments to degrees by scaling it by the calibration factor for the potentiometer and by the reference voltage for the system in accordance with the relationship:

$$\text{ANGLE}(i) = \frac{CF(i)}{V_{REF}} \times [\text{DATA}(i) - \text{ZEROS}(i)]$$

where ANGLE(i) is the angular position of the potentiometer in degrees, CF(i) is the calibration factor for the potentiometer, DATA(i) is the data reading for the potentiometer, ZEROS(i) is the zero reference value for the potentiometer, and $V_{REF}$ is the reference voltage for the computer.

Axial rotation, lateral bending, and anterior-posterior bending are computed by adding the angles of the six potentiometers together as follows:
RIGHT ROTATION=ANGLE(34)
RIGHT SIDE BENDING=ANGLE(35)+ANGLE(36)
FWD AP BENDING=ANGLE(37)+ANGLE(38)+ANGLE (39)
where RIGHT ROTATION is axial rotation, with rotation to the right being considered positive, RIGHT SIDE BENDING is lateral bending, with bending to the right side being considered positive, and FWD AP BENDING is anterior-posterior bending, with forward bending being considered positive.

The screen display is generated in a conventional manner, with the desired parameters displayed along the horizontal and vertical axes. For displays of the type illustrated in FIGS. 13-15, time is displayed along the horizontal axis, with the time base being derived from the system clock in the computer and being scaled in units of seconds per pixel. The other parameters are angles, and they are scaled in units of degrees per pixel.

It should be noted that in the example just given, the data is processed to determine the movement of the subject in terms of rotation only. However, since lengths of the arms between the transducers are known, the data can also be processed to determine translational movement and position of the spine, if desired.

Figure 18:
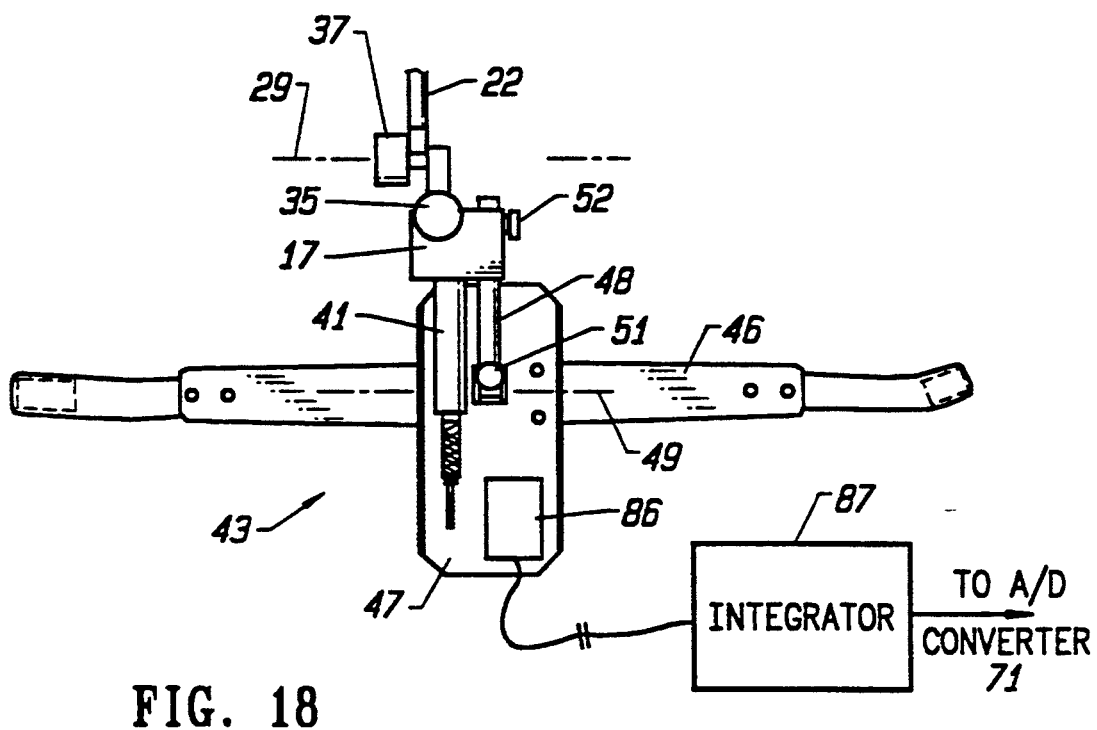
FIG. 18 is a fragmentary plan view similar to a portion of FIG. 1 of another embodiment which is particularly suitable for use in analyzing golf swings.
Figure 19:
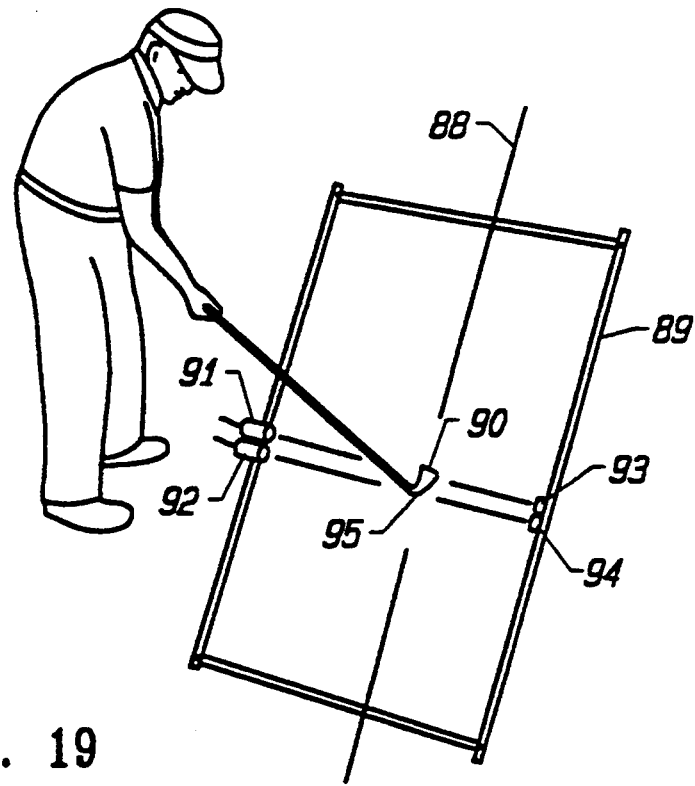
FIG. 19 is a perspective view illustrating the use of the embodiment of FIG. 18 for analyzing the swing of a golfer.

The embodiment illustrated in FIGS. 18-19 illustrates the use of the invention in sport motion analysis, or sports testing, and is specifically adapted for use as a golf swing analyzer. This embodiment is similar to the other embodiments, and in addition includes means for providing information about movement of the golfer's body relative to the ground.

In the embodiment illustrated, information about movement relative to the ground is provided by a gyroscope 86 mounted on the mounting plate 47 affixed to waist belt 46. In one presently preferred embodiment, this transducer is a rate gyroscope which provides a voltage that varies with the angular velocity of the golfer's hips. This voltage is applied to an integrator 87 where it is integrated to provide a signal corresponding to the position of the hips, and this signal is applied to the A/D converter where it is converted to an incremental digital signal with the other transducer signals.

The signal produced by the gyroscope differs from the signals produced by the other transducers in that its reference is an absolute reference which does not change as the golfer swings his club. This enables which enables the transducer to measure movement relative to a target line 88 which in the case of the golf swing tester is a horizontal line in the plane of the desired trajectory of the ball. The other transducers and the linkage in which they are employed all measure relative movement or relative position, with the linkage measuring the motion between the two mounts to which it is attached.

If desired, other types of transducers can be utilized instead of a gyroscope to provide an absolute reference in the golf swing analyzer. One example of such a transducer is an accelerometer which would require double integration to provide a signal corresponding to the position of the golfer's hips. Another example of such a transducer is a potentiometer which is connected to the ground by a suitable linkage.

It is also possible to replace some or all of the potentiometers in the linkage with gyroscopes or other transducers having an absolute reference, in which case some or all of the arms in the linkage can be eliminated.

In the embodiment of FIGS. 18-19, means is also provided for determining when the golfer begins his backswing and when the club impacts the ball. This means includes a pair of photodetectors 91, 92 mounted on a generally rectangular, collapsible frame 89, with mirrors 93, 94 mounted on the frame opposite the photodetectors for reflecting light from sources in the detectors back to sensors in the detectors. The frame is positioned on the ground with the ball 90 interrupting the beam of light between photodetector 91 and mirror 93, and the head of the club 95 interrupting the beam of light between photodetector 92 and mirror 94 as the golfer addresses the ball. As the golfer starts his backswing, the head of the club moves out of the path between photodetector 92 and mirror 94, and that sensor provides a signal. When the club strikes the ball and the ball moves out of the path between photodetector 91 and mirror 93, that sensor provides a signal indicating impact of the club with the ball.

Figure 20:
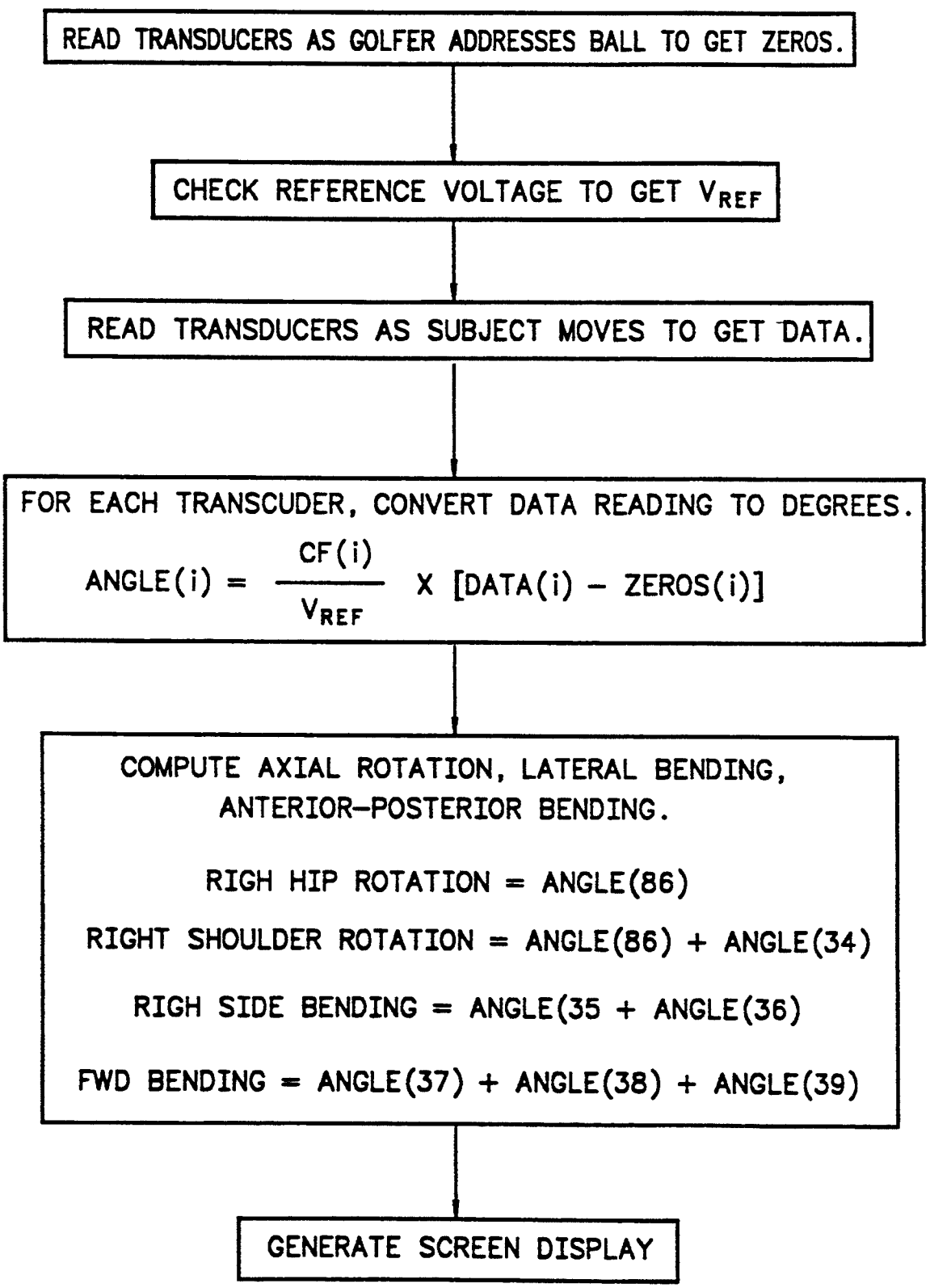
FIG. 20 is a flow chart illustrating the processing of data in the embodiment of FIG. 18.

The flow chart of FIG. 20 illustrates the manner in which the data is processed in the golf swing analyzer. In this embodiment, the zero readings are taken with the golfer addressing the ball, his hips parallel to the target line, ready to begin his backswing. The reference voltage for the computer is checked and stored, and when the backswing begins, as indicated by the signal from photodetector 92, the data collection process begins. During this process, the output of the A/D converter is scanned repeatedly to read the outputs of the gyroscope and the other transducers. The data DATA(86) for the gyroscope is adjusted in a manner similar to the data from the potentiometers and in accordance with the relationship:

$$\text{ANGLE}(86) = \frac{CF(86)}{V_{REF}} \times [\text{DATA}(86) - \text{ZEROS}(86)]$$

where ANGLE(86) is the angular position in degrees of the golfer's hips relative to the target line, CF(86) is the calibration factor for the gyroscope obtained in the same manner as the calibration factors for the potentiometers, DATA(86) is the data reading for the gyroscope, ZEROS(86) is the zero reference value for the gyroscope, and $V_{REF}$ is the reference voltage for the computer.

Hip rotation, shoulder rotation, lateral bending, and anterior-posterior bending are determined from the angles of the gyroscope and the six potentiometers as follows:

RIGHT HIP ROTATION=ANGLE(86)
RIGHT SHOULDER ROTATION=ANGLE(86)+ANGLE(34)
RIGHT SIDE BENDING=ANGLE(35)+ANGLE(36)
FWD AP BENDING=ANGLE(37)+ANGLE(38)+ANGLE(39)

where RIGHT HIP ROTATION is hip rotation relative to the target line, with rotation to the right being considered positive, RIGHT SHOULDER ROTATION is rotation of the shoulders relative to the target line, with rotation to the right being considered positive, RIGHT SIDE BENDING is lateral bending, with bending to the right side being considered positive, and FWD AP BENDING is anterior-posterior bending, with forward bending being considered positive. Rotation of the shoulders relative to the hips is given by ANGLE(34).

Figure 21:
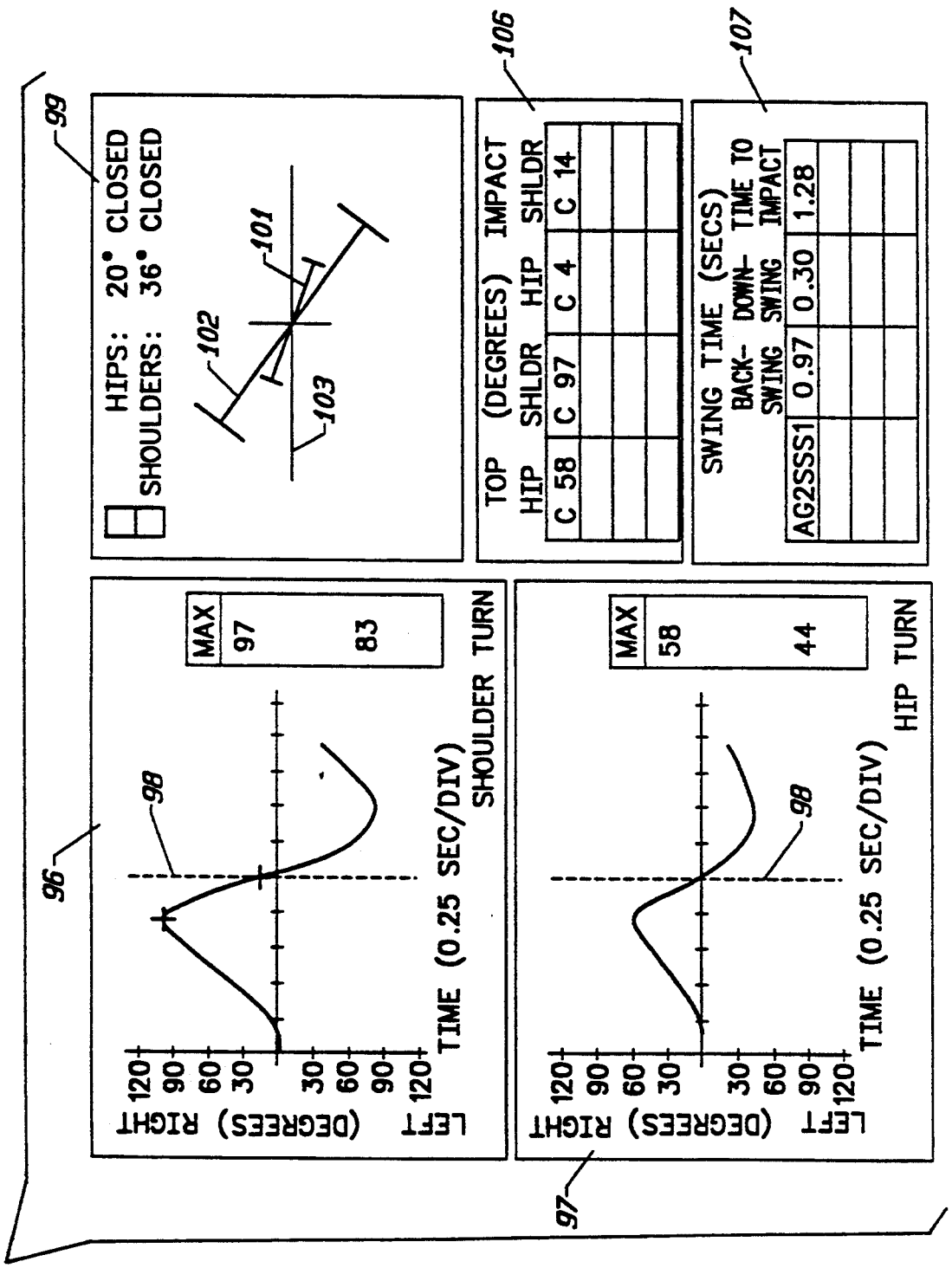
FIGS. 21–24 are examples of video display screens produced by the embodiment of FIG. 18.

An example of the graphical display provided on the monitor screen with the golf swing analyzer is illustrated in FIG. 21. In this particular example, data for only one swing is displayed, but data for any desired number of swings can be displayed in different colors, if desired.

The display shown in FIG. 21 includes a first window 96 in which shoulder rotation (turn) is displayed as a function of time, and a second window 97 in which hip rotation (turn) is displayed as a function of time, with dashed vertical lines 98 indicating the time at which impact occurs. A third window 99 shows the positions of the hips and the shoulders relative to the target line during the swing, with line 101 representing the position of the hips, line 102 representing the position of the shoulders, and line 103 representing the target line. In a fourth window 106, the positions of the shoulders and hips at the top of the swing and at impact with the ball are indicated numerically, with an indication as to whether the hips and shoulders are open or closed. A fifth window 107 displays the backswing time, the downswing time and the time between the start of swing and impact with the ball.

Figure 22:
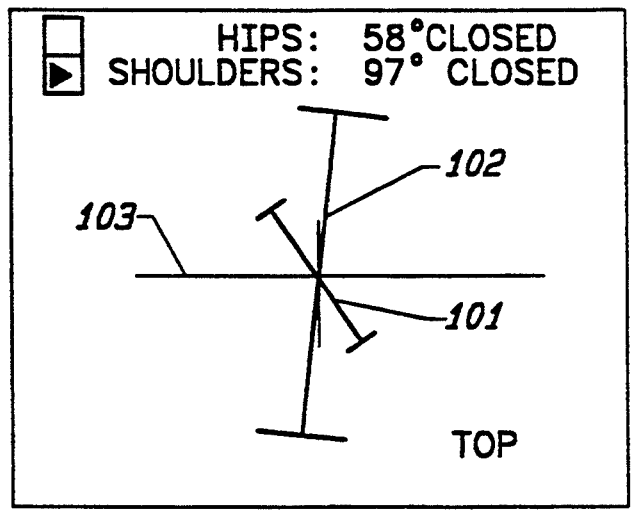
Figure 23:
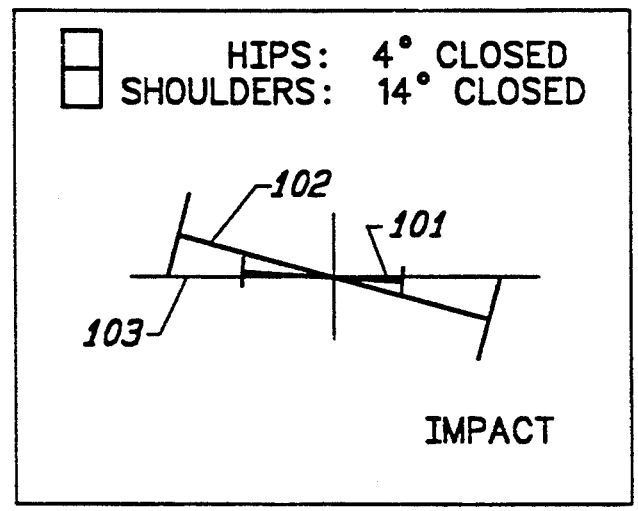
Figure 24:
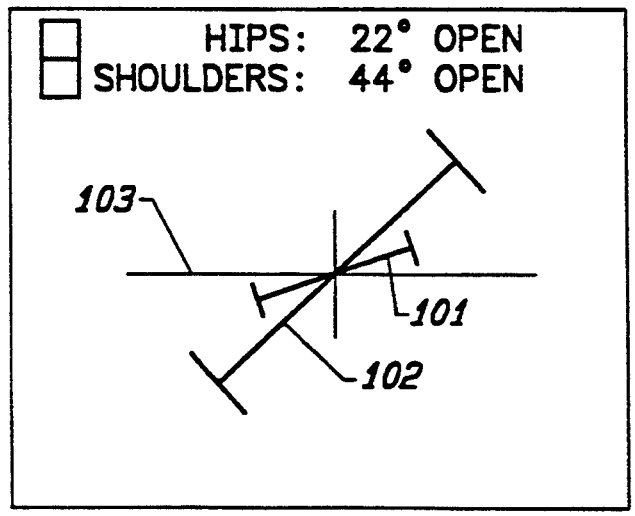

In window 99, the positions of the hips and shoulders are displayed successively at different points during the swing to provide a moving picture of hip and shoulder movement, and examples of displays showing the hips and shoulders at several different points are provided in FIGS. 22-24. FIG. 21 is at a point in the backswing, FIG. 22 is at the top of the backswing, FIG. 23 is at the point of impact with the ball, and FIG. 24 is at a point in the follow-through swing. If desired, the moving display can be stopped at any desired point or points in the swing, e.g. as the top of swing and impact with the ball, to permit detailed analysis of the swing at those points.

The data displayed in the examples of FIGS. 21-24 was obtained with the linkage mounted on the lower portion of the golfer's back, as illustrated in FIG. 19. If desired, a second linkage can be mounted on the upper portion of his back, and measurements can be taken for the entire spine.

The invention has a number of important features and advantages. While the signals from the transducers represent the position of the spine, changes in the signals represent movement of the spine, and by monitoring the changes, important information about the rate and smoothness of spinal motion is obtained, as well as information about the range of such motion. Simultaneous monitoring of all spinal rotations provides a complete biomechanical assessment of spinal motion, and data from different tests can be overlayed for comparative analyses. The system provides a high degree of sensitivity and accuracy and can identify distinct patterns of motion, or "signatures", for different subjects. With the inclusion of a transducer which provides an absolute reference, the system also has significant utility in golf swing analysis and other sports testing applications.

It is apparent from the foregoing that a new and improved spine motion analyzer and method have been provided. While only certain presently preferred embodiments have been described in detail, as will be apparent to those familiar with the art, certain changes and modifications can be made without departing from the scope of the invention as defined by the following claims.

We claim:

1. In a system for analyzing spinal motion of a subject: a linkage having a plurality of arms movable relative to each other in accordance with spinal motion of the subject, at least one potentiometer having an input shaft connected to one of the linkage arms and an electrical resistance which varies in accordance with the position of the shaft, an analog-to-digital converter connected electrically to the potentiometer for providing digital data corresponding to the position of the potentiometer shaft, means for storing a calibration factor corresponding to data produced by the analog-to-digital converter when a calibration voltage is applied to the potentiometer, means for applying a reference voltage to the potentiometer to produce spinal motion data from the analog-to-digital converter corresponding to the spinal motion of the subject, and means for combining the calibration factor with the spinal motion data to provide a spinal motion signal which is substantially independent of differences between the calibration voltage and the reference voltage.

2. The system of claim 1 wherein the calibration factor is provided in accordance with the following relationship:

$$CF = \frac{POT}{ADI} \times V_{CAL},$$

where CF is the calibration factor, POT is the angular position of the potentiometer shaft, $V_{CAL}$ is the calibration voltage, and ADI is the data produced by the analog-to-digital converter when the calibration voltage is applied, and the calibration factor is combined with the spine motion data in accordance with the following relationship:

$$ANGLE = \frac{CF}{V_{REF}} \times DATA,$$

where ANGLE is the output signal, CF is the calibration factor, DATA is the spine motion data from the analog-to-digital converter, and $V_{REF}$ is the reference voltage.

3. In a sports motion analyzer: a first transducer providing an electrical signal corresponding to rotational movement of a first part of a person's body relative to the ground, a linkage having a plurality of arms connected together and adapted to be connected between the first part of the body and a second part of the body, transducer means coupled to the linkage arms for providing electrical signals corresponding to motion of the second part of the body relative to the first part, a display, and means responsive to the electrical signals for providing visual representations of the motion of the first and second parts of the body on the display.

4. The sports motion analyzer of claim 3 wherein the first transducer is a gyroscope.

5. The sports motion analyzer of claim 3 wherein the linkage is adapted to be mounted between the person's hips and shoulders, and the means for providing a visual representation includes means for providing graphical representations of the hip and shoulder rotation of the person.

6. The sports motion analyzer of claim 3 wherein the means for providing a visual representation also includes means for providing graphical representations of the person's lateral bending and anterior-posterior bending.

7. In a system for analyzing the motion of a golfer swinging a club: a first transducer adapted to be attached to the golfer's hips providing an electrical signal corresponding to rotational movement of the golfer's hips relative to the ground, a linkage having a plurality of arms connected together between the golfer's hips and shoulders, transducer means coupled to the linkage arms for providing electrical signals corresponding to spinal motion of the golfer, and means responsive to the electrical signals for providing visual information about the motion of the golfer's hips, shoulders and spine.

8. The system of claim 7 wherein the first transducer is a gyroscope.

9. The system of claim 7 wherein the means for providing visual information includes a video display screen, and means for providing graphical representations of hip and shoulder rotation of the golfer on the screen.

10. The system of claim 7 wherein the means for providing a visual representation also includes means for providing graphical representations of the golfer's lateral bending and anterior-posterior bending.

* * * * *